United States Patent
Pang

(10) Patent No.: US 6,204,360 B1
(45) Date of Patent: Mar. 20, 2001

(54) RETRO-INVERSO THYMOSIN ALPHA 1 HYBRIDS

(75) Inventor: Danny Zhong Der Pang, Fullerton, CA (US)

(73) Assignee: USA Universe Bioengineering, Inc., Anaheim, CA (US)

( * ) Notice: Subject to any disclaimer, the term of this patent is extended or adjusted under 35 U.S.C. 154(b) by 0 days.

(21) Appl. No.: 09/465,025

(22) Filed: Dec. 16, 1999

(51) Int. Cl.[7] ............... A61K 38/00; A61K 31/00; C07K 5/00; C07K 7/00
(52) U.S. Cl. ............ 530/324; 530/325; 530/326; 530/327; 530/328; 530/329; 514/12; 514/13; 514/14; 514/15; 514/16; 424/449; 424/448; 424/22
(58) Field of Search ............... 424/449; 514/22, 514/2, 1, 169; 604/20; 530/324; 536/23.1

(56) References Cited

PUBLICATIONS

Van Regenmortel et al., "D–peptides as immuogens and diagnostic reagents", Current Opinion in Biotechnology, vol. 9 (4), pp. 377–382, 1998.*

Vunnam et al., "Synthesis and Study of normal, enatio, retro, and retroenantio isomers of cecropin A–melittin hybrids, their end group effects and selective enzyme inactivation", Journal of Peptide Research, vol. 51 (1), pp. 38–44, 1998.*

The Merck Index, Eleventh Edition; Budarvari, S., Editor; Merck & Co., Inc., Rahway, NJ, 1989.*

Dintzis et al., "A Comparison of the Immunogenicity of a pair of enantiomeric proteins", Proteins: Structure, Function, and Genetics, vol. 16, pp. 306–308, 1993.*

* cited by examiner

*Primary Examiner*—Karen Cochrane Carlson
*Assistant Examiner*—Patricia A. Robinson

(57) ABSTRACT

Retro-inverso thymosin alpha 1 and its hybrids, native/retro-inverso thymosin alpha 1, possess the characteristics of greater stability and activity than their parent thymosin alpha 1. Such novel analogs and hybrids are useful for therapeutic purposes in viral, neoplastic and immunodeficiency diseases.

2 Claims, No Drawings

SEQUENCE LISTING

<160> NUMBER OF SEQ ID NOS: 2

<210> SEQ ID NO 1
<211> LENGTH: 28
<212> TYPE: PRT
<213> ORGANISM: Synthetic
<220> FEATURE:
<221> NAME/KEY: D-amino Acids
<222> LOCATION: 1 to 28
<223> OTHER INFORMATION: D-amino Acids in the Sequence

<400> SEQUENCE: 1

Asn Glu Ala Glu Glu Val Val Glu Lys Lys Glu Lys Leu Asp Lys
1               5                   10                  15

Thr Thr Ile Glu Ser Ser Thr Asp Val Ala Ala Asp Ser
                20                  25

<210> SEQ ID NO 2
<211> LENGTH: 56
<212> TYPE: PRT
<213> ORGANISM: Synthetic
<220> FEATURE:
<221> NAME/KEY: D-amino Acids
<222> LOCATION: 29 to 56
<223> OTHER INFORMATION: D-amino Acids in the Sequence

<400> SEQUENCE: 2

Ser Asp Ala Ala Val Asp Thr Ser Ser Glu Ile Thr Thr Lys Asp
1               5                   10                  15

Leu Lys Glu Lys Lys Glu Val Val Glu Glu Ala Glu Asn Asn Glu
                20                  25                  30

Ala Glu Glu Val Val Glu Lys Lys Glu Lys Leu Asp Lys Thr Thr
                35                  40                  45

Ile Glu Ser Ser Thr Asp Val Ala Ala Asp Ser
                50                  55

RETRO-INVERSO THYMOSIN ALPHA 1 HYBRIDS

BACKGROUND OF THE INVENTION

This invention relates to a retro-inverso analogue of thymosin alpha1 and its hybrids, native/retro-inverso thymosin alpha 1 hybrids, which are immunomodulators with high resistance to enzymatic hydrolysis and have prolonged in vivo activity, and pharmaceutical compositions containing them and methods for using them.

A standard cell-free protein extract preparation from the thymus gland, known as thymosin fraction V (TF5) (U.S. Pat. No. 4,082,737), was demonstrated to be a potent immunopotentiating preparation. TF 5 can suppress to various extents immune deficiency diseases and can also act in lieu of the thymus gland to reconstitute immune functions in thymic deprived and/or immunodeprived individuals (Wara et al., N. Engl. J. Med 292: 70, 1975). Analytical polyacrylamide gel electrophoresis and isoelectric focusing have demonstrated that TF5 consists of a number of polypeptides termed thymosin, with molecular weights ranging from 1,000 to 15,000.

The first of these peptides to be purified to homogeneity and sequenced from TF5 was called thymosin alpha 1 (TM-alpha1) (Goldstein et al., Proc. Natl. Acad. Sci. 74:725, 1977; U.S. Pat. No. 4,079,127). The chemical synthesis of TM-alpha1 by solution and solid phase synthesis techniques is described in U.S. Pat. Nos. 4,148,788 and 5,856,440. Identical to the native TM-alpha1 in the biological potent and amino acid sequence with the lack of the N-terminal acetyl group, recombinant TM-alpha1 can be produced in E. coli by recombinant DNA cloning techniques (Wetzel et al., Biochemistry 19:6096, 1980). TM-alpha1 analogs and derivatives also have been produced, U.S. Pat. Nos. 4,116, 951 and 5,512,656. TM-alpha1 is a 28 amino acid acidic peptide with a molecular weight of 3,100 and a pI in the range of 4.0–4.3. TM-alpha1 maintains many of the biologic effects of TF5 and has been found to be 10 to 1,000 times more active than TF5 in a number of bioassay systems designed to measure the maturation and function of T lymphocytes.

TM-alpha1 potentiates the immune system by stimulating alpha- and gamma-interferon production, increasing production of T-cell growth factor and macrophage migration inhibitory factor, increasing T-cell numbers, inducing lymphocyte maturation and differentiation and expression of interleukin-2 receptors, and improving T-cell helper cell activity (Marshall et al., J. Immunol. 126:741, 1981; Mutchnick et al., Clin. Immunol. Immunopathol. 23:626, 1982; Low et al., Thymus 6:27,1984; Sztein et al., Proc. Natl. Acad. Sci. U.S.A. 83:6107, 1986; Serrate et al., J. Immunol. 1939:2338,1987; Baxevanis et al., Immunopharm. 13:133, 1987). TM-alpha1 is currently undergoing clinical trials in the U.S.A. as an immunomodulator in cancer patients, in individuals with chronic active hepatitis B, and as an immunoenhancer of vaccines in immunocompromised individuals. (Goldstein, A. L., Cancer Invest. 12:545, 1994; Lopez et al., Ann. Oncol. 5:741, 1994; Garaci et al., Eur. J. Cancer. 31A:2403,1995; Garaci et al., Mech. Ageing. Dev. 96:103, 1997; Bonkovsky, H. L., Hepatology 26(3 Suppl 1):143S, 1997; Liaw, Y. F., J. Gastroenterol. Hepatol. 12:S346, 1997). TM-alpha1 has been approved for use in the treatment of hepatitis B in many Asian countries.

However, like most endogenous and exogenous biologically active peptides, which are highly susceptible to proteolysis by naturally occurring aminopeptidases, TM-alpha1 also has a short half-life in vivo (Rost, K., Int. J. Clin. Pharmacol. Ther. 37:51, 1999).

Therefore, there remains a need to find new derivatives of TM-alpha1 that exhibit greater stability and activity.

BRIEF SUMMARY OF THE INVENTION

The present invention relates to a retro-inverso analogue of TM-alpha1 and its hybrids, native/retro-inverso TM-alpha1 hybrids. The native/retro-inverso TM-alpha1 hybrids of this invention are represented by the following formulas:

T-T' or T-L-T'

T is TM-alpha1; T' is a retro-inverso analogue of TM-alpha1 composed of all-D amino acids and having a sequence of: D-Asn-D-Glu-D-Ala-D-Glu-D-Glu-D-Val-D-Val-D—Glu-D-Lys-D-Lys-D-Glu-D-Lys-D-Leu-D-Asp-D-Lys-D-Thr-D-Thr-D-Ile-D-Glu-D—Ser-D-Ser-D-Thr-D-Asp-D-Val-D-Ala-D-Ala-D-Asp-D-Ser (SEQ ID NO:1); L is a chemical or peptide linker. TM-alpha1 is linked to the retro-inverso analogue of TM-alpha1 either directly or through a linker in a C-terminal to N-terminus fusion. TM-alpha1 is fused to retro-inverso analogue of TM-alpha1 in such a manner as to produce a hybrid peptide with a sequence of: Ac-Ser-Asp-Ala-Ala-Val-Asp-Thr-Ser-Ser—Glu-Ile-Thr-Thr-Lys-Asp-Leu-Lys-Glu-Lys-Lys-Glu-Val-Val-Glu-Glu-Ala-Glu-Asn-D—Asn-D-Glu-D-Ala-D-Glu-D-Glu-D-Val-D-Val-D-Glu-D-Lys-D-Lys-D-Glu-D-Lys-D-Leu—D-Asp-D-Lys-D-Thr-D-Thr-D-Ile-D-Glu-D-Ser-D-Ser-D-Thr-D-Asp-D-Val-D-Ala-D—Ala-D-Asp-D-Ser-OH (SEQ ID NO:2).

The analogs and hybrids of the present invention, with their distinguishing chemical structure formula, have greater stability and activity than their parent TM-alpha1. Such analogs and hybrids (1) are resistant to proteolytic degradation by naturally occurring proteases; (2) do not elicit an imrnune response comparable to that elicited by TM-alpha1; (3) prolong their activity in vivo, thus enhancing their pharmacologic functions, and (4) have the characteristics of being unique to viral, neoplastic and immunodeficiency diseases and are useful for therapeutic purposes.

BRIEF DESCRIPTION OF THE SEVERAL VIEWS OF THE DRAWING

Not Applicable.

DETAILED DESCRIPTION OF THE INVENTION

The present invention is directed to retro-inverso analogue of TM-alpha1 and its hybrids, native/retro-inverso TM-alpha1 hybrids.

1. Definition

In describing the present invention, the following terms are intended to be defined as indicated below.

In the sequences of the compounds of the present invention as given above and in the description which follows, Ser stands for the L-serine residue and similarly, Asp for L-aspartic acid, Ala for L-alanine, Val for L-valine, Thr for L-threonine, Glu for L-glutamic acid, Ile for L-isoleucine, Lys for L-lysine, Leu for L-lucine, Asn for L-asparagine, Gly for glycine; D-Ser for D-serine, D-Asp for D-aspartic acid, D-Ala for D-alanine, D-Val for d-valine, D-Thr for D-threonine, D-Glu for D-glutamic acid, D-Ile for D-isoleucine, D-Lys for D-lysine, D-Leu for D-lucine, D-Asn for D-asparagine.

"Native" peptides refer to peptides recovered from a source occurring in nature. The term "TM-alpha1" would include naturally occurring TM alpha1 and fragments thereof.

"All-L peptides" refer to peptides composed of all-L amino acids. The all-L peptides form right-handed helices.

"All-D peptides" refer to peptides composed of all-D amino acids. The all-D peptides form left-handed helices.

"Retro" peptides refer to peptides derived from the parent peptide in a backwardly read sequence. Retro peptide starts from the C-termiinus to the N-terminus of the parent peptide backbone. When a linear random retro peptide chain is viewed from the opposite end by rotating the peptide in the plane 180 degrees, its amino acid side chains will project to the opposite side of the peptide chain and topologically resemble D-amino acid residues as compared to the parent all-L peptide. Therefore, the homology between retro-sequence and its parent is generally very low.

"Inverso" peptides refer to an all-D or enantio peptides, which are derived from the parent all-L peptides in the same sequence. The peptide is the D enantiomer of the all-L peptide.

"Retro-inverso" peptides refer to retro-all-D or retroenantio peptides, assembling D-amino acid residues in the reverse sequence from that in the parent peptides. When viewed a linear random retro-inverso peptide chain from the opposite end by rotating the peptide in the plane 180 degrees, the amino acid side chains will project to the same side as those of the parent all-L peptide. A retro-inverso peptide will therefore have the same sequence and the same side chain topology as the parent, but the amide bonds and helix dipole directions and the charge on the end groups will be reversed.

"Hybrid" peptides refer to peptides formed by the fusion of two different peptides. A native/retro-inverso hybrid peptide is a peptide in which part of the chain of amino acids comes from the native peptide sequence and some from the retro-inverso analog of the native peptide.

2. Thymosin Alpha 1

The term thymosin alpha 1 (TM-alpha1) refers to proteins having amino acid sequences which are substantially similar to the native human TM-alpha1 amino acid sequences and which are biologically active in that they are capable of binding to thymosin receptors, transducing a biological signal initiated by binding TM-alpha1 receptors, or cross-reacting with anti-TM-alpha1 antibodies raised against TM-alpha1. Such sequences are disclosed, for example, in U.S. Pat. No. 4,079,127.

3. Retro Analogs of TM-alpha1

The term retro analogs of alpha1 (Retro-TM-alpha1) refer to peptides having the backwardly read amino acid sequences of the native TM-alpha1. Although retro-TM-alpha1 has the same amino acid composition and the same hydrophobicity profile as TM-alpha1, the sequence homology between retro-TM-alpha1 and TM-alpha1 is very low because the sequences are inverted. When viewed from the opposite end by rotation in the plane 180 degrees, retro-TM-alpha1 will be the same sequence as the parent TM-alpha1 with reversed amide bond and helical dipole directions and charge on the end groups, and its amino acid side chains will project to the opposite side of the peptide chain and topologically resemble D-amino acid residues as compared to the parent TM-alpha1. Therefore, retro-TM-alpha1 is topologically related to inverso analog of TM-alpha1. They could be linked to form novel retro/inverso TM-alpha1 hybrids that contain two topologically superimposable molecules.

Circular Dichroism analyses revealed that the ellipticities of retro peptides and their native counterparts were similar but not identical because the sequences are inverted (Juwadi et al., *J. Peptide Res.*, 53:244, 1999; Olszewski K. *Protein Engineering*, 9:5, 1996). Sequence is a critical structural feature in peptides and plays an important role in its activity (Merrifield et al., *Proc. Natl. Acad. Sci. USA*, 92:3449, 1995). Recent studies also demonstrated that the sequence and helix dipole together are essential structural features for the activities of normal and retro ceropin-melittin hybrids against all the test bacteria (Juwadi et al., *J. Peptide Res.*, 53:244, 1999).

4. Inverso Analogs of TM-alpha1

The term inverso analogs of TM-alpha1 (Inverso-TM-alpha1) refer to peptides composed of all-D amino acids in the same amino acid sequences as TM-alpha1. Inverso-TM-alpha1 is the D enantiomer of the native TM-alpha1 and is subject to the same conformational constraints as the native TM-alpha1. In the inverso-TM-alpha1 structure, the normal right-handed helical segments found in the native TM-alpha1 become the left-handed helices and the entire folded chains are mirror images. Inverso-TM-alpha1 and the native TM-alpha1 will not have the same topology and would not be expected to interact with a natural chiral receptor. However, studies have indicated that all-D- and all-L-enantiomers of several of the ceropin-melittin hybrids were equally potent against all of the bacterial strains tested, indicating that chirality is not critical and need not be the same as the all-L parent petide and that the peptides do not finction by chiral interactions with receptors, enzymes or chiral lipids (Wade et al., *Proc. Natl. Acad. Sci. USA*, 87:4761, 1990; Merrifield et al., *Proc. Natl. Acad. Sci. USA*, 92:3449,1995). The ellipticities of the D- and L-peptides were similar in magnitude but opposite in sign. The all-D-peptides formed left-handed helices and had positive molar ellipticities at 222 nm, whereas all-L-peptides formed hight-handed helices and had negative molar ellipticities (Vunnam et al., *J. Pept. Res.*, 51:38, 1998).

Since inverso-TM-alpha1 is not of the natural handedness (not of the chirality as they occur in nature or as the native TM-alpha1), inverso-TM-alpha1 is more resistant to proteolytic degradation by naturally occurring aminopeptidases than TM-alpha1. As an all-D peptide, inverso-TM-alpha1 does not elicit an immune response comparable to that elicited by TM-alpha1 (Dintzis et al., Proteins, 16:306, 1993).

5. Retro-inverso Analogs of TM-alpha1

The term retro-inverso analogs of alpha1 (Retro-inverso-TM-alpha1) refer to the retro analogs of TM-alpha1 in the all-D configuration, having a sequence of: H-D-Asn-D-Glu—D-Ala-D-Glu-D-Glu-D-Val-D-Val-D-Glu-D-Lys-D-Lys-D-Glu-D-Lys-D-Leu-D-Asp-D-L ys-D-Thr-D-Thr-D-Ile-D-Glu-D-Ser-D-Ser-D-Thr-D-Asp-D-Val-D-Ala-D-Ala-D-Asp-D—Ser-OH (SEQ ID NO:1). When a retro-inverso-TM-alpha1 chain is viewed from the opposite end by rotating the peptide in the plane 180 degrees, its amino acid side chains will project to the same side as those of the parent all-L TM-alpha1. Therefore, a retro-inverso-TM-alpha1 will have the same sequence and the same side chain topology as its parent TM-alpha1, but with the directions of the amide bonds and helix dipole and the charge on the end groups reversed.

Studies of antigenicity of topochemically related peptides have demonstrated that antigenic cross-recognition is found not only between the parent peptide and its retro-inverso derivative, or between the inverso and the retro derivatives, but also with the complete series of topologically related peptides, implying that related topology of the peptide side chains contributes to the cross-reactivity. The findings also pointed out that the charge difference at the chain termini between linear antigens and the corresponding retro-form (amino group substituted by a carboxyl group) does not have a prominent role in the cross-recognition (Verdoliva et al., *Biochimica et Biophysica Acta*, 1253:57, 1995). Another study of retro-inverso analogue of MHC (major histocompatibility complex) concluded that the T cell receptors of T cells primed in vivo with the retro-inverso analogues readily cross-react with parent and retro-inverso analogue-MHC complexes, indicating that the retro-inverso peptides, containing changes involving the backbone and not the orientation of side chains, function like the parent (Meziere et al., *J. Immunol.*, 159:3230, 1997).

The chemical synthesis of retro-inverso peptides by solution and solid phase synthesis techniques is described in U.S. Pat. Nos. 4,732,890 and 5,218,089, and by Bonelli et al., *Int. J. Pept. Protein Res.*, 24:553, 1984; Hernandez et al., *J. Med. Chem.*, 31:1825, 1988 and Briand et al., *Proc. Natl. Acad. Sci. U.S.A.*, 94:12545,1997. Retro-inverso analogs of thymopentin have been demonstrated to possess longer half-life and immunomodulatory effects in vivo than the parent, as disclosed in U.S. Pat. Nos. 5,218,089 and 5,200,506.

Peptides corresponding to the immunodominant loop located at residues 135–158 on capsid protein VP1 of foot-and-mouth disease virus (FMDV) generally elicit high levels of anti-peptide and virus-neutralizing antibodies. But its retro-inverso analogue induced greater and longer-lasting antibody titers than did the corresponding L-peptide (Briand et al., *Proc. Natl. Acad. Sci. U.S.A.*, 94:12545, 1997). Retro-inverso analogues of MHC II restricted peptides that contained the correct orientation of the side chains but an inverse main chain was not recognized by antibodies raised against the native peptide and did not elicit antibodies when injected into BALB/c mice. Those retro-inverso peptides appear to be poor immunogens as a result of their weak capacity to bind to MHC II molecules (Herve et al., *Mol. Immunol.*, 34:157, 1997).

For relating to TM-alpha1 topologically, retro-inverso-TM-alpha1 can function like TM-alpha1. Since its inverted chiral configuration in the retro-inverso-TM-alpha1 is not easily recognized by enzymes, retro-inverso-TM-alpha1 is particularly stable to proteolytic treatments, making retro-inverso-TM-alpha1 and its derivatives useful for their prolonged half-life in vitro and in vivo. Unlike TM-alpha1, retro-inverso-TM-alpha1 does not elicit antibodies, when used by injection, against retro-inverso-TM-alpha1 and is not expected to trigger undesirable humoral responses such as hypersensitivity or allergic disease.

Retro-inverso-TM-alpha1 of the present invention provides the modified peptides with higher resistance to proteolytic degradation and with enhanced pharmacological properties. Retro-inverso-TM-alpha1 of this invention may be produced by any of the conventional organic synthetic processes used for producing peptides, such as the liquid-phase or solid-phase method.

6. Native/retro-inverso TM-alpha1 Hybrids

Native/retro-inverso TM-alpha1 hybrids refer to hybrid peptides in which part of the chain of amino acids comes from TM-alpha1 and some from the retro-inverso analog of TM-alpha1.

The native/retro-inverso TM-alpha1 hybrids of the present invention are synthesized chemically in which the C-terminal portion of TM-alpha1 is fused to the N-terminal portion of retro-inverso-TM-alpha1. TM-alpha1 is fused to retro-inverso analog of TM-alpha1 either directly or through a linker. Specifically, the compounds of the present invention are represented by the following formulas:

T-T' or T-L-T'

T is TM-alpha1; T' is retro-inverso-TM-alpha1 composed of all-D amino acids and having a sequence of: D-Asn-D-Glu-D-Ala-D-Glu-D-Glu-D-Val-D-Val-D-Glu-D-Lys-D—Lys-D-Glu-D-Lys-D-Leu-D-Asp-D-Lys-D-Thr-D-Thr-D-Ile-D-Glu-D-Ser-D-Ser-D-Thr—D-Asp-D-Val-D-Ala-D-Ala-D-Asp-D-Ser (SEQ ID NO:1); L is a chemical or peptide linker. TM-alpha1 is fused to retro-inverso-TM-alpha1 in such a manner as to produce a compound with a sequence of: Ac-Ser-Asp-Ala-Ala-Val-Asp-Thr-Ser-Ser-Glu-Ile-Thr—Thr-Lys-Asp-Leu-Lys-Glu-Lys-Lys-Glu-Val-Val-Glu-Glu-Ala-Glu-Asn-D-Asn-D-Glu—D-Ala-D-Glu-D-Glu-D-Val-D-Val-D-Glu-D-Lys-D-Lys-D-Glu-D-Lys-D-Leu-D-Asp-D—Lys-D-Thr-D-Thr-D-Ile-D-Glu-D-Ser-D-Ser-D-Thr-D-Asp-D-Val-D-Ala-D-Ala-D-Asp—D-Ser-OH (SEQ ID NO:2).

Unless otherwise specified, the terms native/retro-inverso hybrids of TM-alpha1 refer to hybrid peptides without a linker added.

The native/retro-inverso TM-alpha1 hybrids of the present invention, with their distinguishing chemical structure formulas, are not TM-alpha1 dimers, although they may be projected to TM-alpha1 dimers when the retro-inverso-TM-alpha1 chain is viewed from the opposite end by rotating the peptide in the plane 180 degrees. TM-alpha1 and retro-inverso-TM-alpha1 within the hybrid possess different conformational constraints with respect to the helical orientation of two peptides. TM-alpha1 forms right-handed helices, while the retro-inverso-TM-alpha1 forms left-handed helices. Native/retro-inverso TM-alpha1 hybrids with both right-handed and left-handed geometries possess many greater advantageous properties than its parent TM-alpha1. Such hybrids (1) are resistant to proteolytic degradation by naturally occurring proteases; (2) do not elicit an immune response comparable to that elicited by TM-alpha1; (3) prolong their activity in vivo; (4) enhance their pharmacologic functions since they contain two topologically superimposable molecules of TM-alpha1; and (5) have the characteristics of being unique to viral, neoplastic and immununodeficiency diseases and are useful for therapeutic purposes.

An example of hybrids comprising TM-alpha1 and retro-inverso analogue of TM-alpha1 is shown in the accompanying Sequence Listing. The hybrid comprises TM-alpha1 (amino acids 1–28) linked directly to retro-inverso analogue of TM-alpha1 (amino acids 29–56), as shown in SEQ ID NO:2.

Equivalent hybrids may vary from the sequence of SEQ ID NO:2 by one or more substitutions, deletions, or additions, the net effect of which is to retain biological activity of the peptide when derived as a compound comprising TM-alpha1 and retro-inverso analog of TM-alpha1.

7. Peptides and Analogs

The present invention provides retro-inverso-TM-alpha1 and its hybrids, native/retro-inverso TM-alpha1 hybrids. Derivatives and analogs of the retro-inverso-TM-alpha1 and native/retro-inverso TM-alpha1 hybrids of the present invention may also be obtained by modifying the primary amino acid structure with other chemical moieties, by mutations, by linking particular functional groups to amino acid side chains or at the N- or C-termini, by substitution with D-amino acids in TM-alpha1 of the hybrid, by replacing TM-alpha1 of the hybrid with inverso analogue of TM-alpha1, or by conjugating with other proteins or polypeptides. Bioequivalent analogs of the retro-inverso-TM-alpha1 and its hybrids may also be constructed by making various substitutions of residues or sequences.

Retro-inverso-TM-alpha1 and native/retro-inverso TM-alpha1 hybrid compositions can be prepared for administration by combining retro-inverso-TM-alpha1 or native/retro-inverso TM-alpha1 hybrid having the desired degree of purity and the pharmaceutically effective amount with physiologically acceptable carriers.

Retro-inverso analogue of TM-alpha1 and native/retro-inverso TM-alpha1 hybrids may be used to enhance proliferation, maturation and functional activation of T cells, or to enhance antiviral, antiproliferative and immunomodulatory effects. Specifically, compositions containing retro-inverso analogue of TM-alpha1 or native/retro-inverso TM-alpha1 hybrid may be used to enhance the immune system to battle against viral, neoplastic and immunodeficiency diseases. To achieve this result, a pharmaceutically effective quantity of a hybrid peptide composition is administered to a mammal, preferably a human, in association with a pharmaceutically acceptable carrier.

The retro-inverso-TM-alpha1 and native/retro-inverso TM-alpha1 hybrids of the invention can be administered by injections with a pharmaceutically acceptable diluent.

The retro-inverso-TM-alpha1 and native/retro-inverso TM-alpha1 hybrids of the invention can also be used orally by the means of a lozenge or the like, or directly to the nasal mucosa or bronchus by means of an inhaler or the like, or in the form of external preparations with penetration enhancers.

The retro-inverso-TM-alpha1 and native/retro-inverso TM-alpha1 hybrids within the scope of the present invention can be synthesized by any of the conventional organic synthetic processes used for producing peptides, such as the liquid-phase or solid-phase method. The synthesis may be carried out by manual techniques or automatically using, for example, an Applied Biosystems 430A Peptide Synthesizer (Foster City, Calif.) or an Advanced Chem Tech Model 90 tabletop peptide synthesizer (Advanced Chem Tech, Louisville, Ky.), following the instructions in the instruction manual provided by the manufacturer. The peptide synthesis starts from the carboxy-terminal end of the peptide using an alpha-amino protected amino acid. Examples are described below.

The following examples are offered to further illustrate the invention, but they are not intended to be limitative thereof:

EXAMPLE 1

Retro-inverso-TM-alpha1:

Retro-inverso-TM-alpha1 was synthesized, in analogy to routine Fmoc-SPPS (solid phase peptide synthesis), by the stepwise addition of base labile Fmoc-amino protected amino acids to Wang (p-benzyloxybenzyl alcohol) resin (Wang, S. S., *J. Am. Chem. Soc.*, 95:1328, 1973). Pre-loaded Fmoc-D-Ser(But)-Wang resin was used as a starting point for the synthesis. 1.0 gm of Fmoc-D-Ser(But)-Wang resin (Advanced Chem Tech, Louisville, Ky.) (0.6 mmol/g) was suspended in 15 volumes of 100% N,N-dimethylformanide (DMF) in a peptide synthesis flask and allowed to swell for 30 minutes at room temperature. The solid phase peptide synthesis was then performed in the following steps wherein in accordance with the desired sequence one amino acid was successively coupled to the resin-bound amino acid or the growing peptide chain on the resin in each synthetic cycle. This synthetic cycle is repeated until the desired peptide is assembled in the resin. Fmoc-amino acid corresponds to the N-terminal amino acid. Fmoc-amino acids, whose amino group, carboxyl group and/or hydroxyl group is protected with appropriate protective groups, are activated at its alpha carboxyl group by creating the 1-hydroxybenzotriazole (HOBt) ester in situ with HOBt and 1,3-Diisopropylcarbodiimide (DIC) or 2-(1H-Benzotriazole-1-yl)-1,1,3,3-Tetramethyl-uroniumhexafluro-phosphate (HBTU) in N,N-dimethylformanide (DMF) or N-methyl-2-pyrrolidinone (NMP). One hour coupling times and double coupling were used in all amino acid couplings. 15 volumes of solvent or reagents were used for each washing. All amino acid derivatives used were of D-configuration unless otherwise indicated:

1. Wash twice with 100% DMF;
2. Stir for 5 minutes with 25% piperidine in DMF;
3. Stir for 20 minutes with 25% piperidine in DMF;
4. Wash twice with 100% DMF;
5. Wash twice with 100% dichloromethane (DCM);
7. Wash twice with 100% DMF;
8. Stir for 60 minutes with 2.0 mmol each of Fmoc-D-Asp (OBUt)-OH, HOBt, and DIC in NMP;
9. Stir for 60 minutes with 2.0 mmol each of Fmoc-D-Asp (OBUt)-OH, HOBt, and HBTU, and N,N'-Diisopropylethylamine (DIPEA) in NMP;
10. Wash twice with 100% DMF;
11. Wash twice with 100% DCM;
12. The coupling reaction was monitored for completeness in each cycle of addition by Kaiser test (ninhydrin color reaction) (Sarin et al., *Analytical Biochemistry*, 117:147, 1981) to determine free amine. If the reaction shows positive (blue color), repeat steps 8–12; if no color, go to the next cycle.

The peptide chain elongation cycle was continued in the same manner by using Fmoc-amino acids and one amino acid was incorporated into the growing peptide at a time in step 8 of each synthetic cycle in the following order: Fmoc-D-Ala-OH.H.sub.2 O, Fmoc-D-Ala-OH.H.sub.2 O, Fmoc-D-Val-OH, Fmoc-D-Asp(OBut)-OH, Fmoc-D-Thr(But)-OH, Fmoc-D-Ser(But)-OH, Fmoc-D-Ser(But)-OH, Fmoc-D-Glu(OBut)-OH, Fmoc-D-Ile-OH, Fmoc-D-Thr(But)-OH, Fmoc-D-Thr(But)-OH, Fmoc-D-Lys(Boc)-OH, Fmoc-D-Asp(OBut)-OH, Fmoc-D-Leu-OH, Fmoc-D-Lys(Boc)-OH, Fmoc-D-Glu(OBut)-OH, Fmoc-D-Lys(Boc)-OH, Fmoc-D-Lys(Boc)-OH, Fmoc-D-Glu(OBut)-OH, Fmoc-D-Val-OH, Fmoc-D-Val-OH, Fmoc-D-Glu(OBut)-OH, Fmoc-D-Glu(OBut)-OH, Fmoc-D-Ala-OH.H.sub.2 O, Fmoc-D-Glu(OBut)-OH and Fmoc-D-Asn(Trt)-OH. After completion of the final coupling reaction, the N.sup.alpha deprotection reaction was carried out by stirring the protected retro-inverso-TM-alpha1-Wang resin with 25% piperidine in DMF for 5 and 20 minutes, respectively. Cleavage and deblocking of the side chains of the retro-inverso-TM-alpha1 was accomplished with 95% trifluoroacetic acid (TFA), 2.5% triisopropysilane (TIS) in distilled water for 4 hours at room temperature. Cleaved peptide was separated from resin by filtration (0.22 .mu.m filter) and partial purification was obtained by precipitation using 10 times volumetric excess of cold ether. The precipitated peptide was washed several times with ether and allowed to dry. Crude peptides are subjected to gel filtration followed by HPLC (high-performance liquid chromatography) purification. Retro-inverso-TM-alpha1 was purified by semi-preparative HPLC on a 25 cm octadecyl silane column (Vydac, Hisperia, Calif.) to give 80 mg of H-D-Asn-D-Glu-D-Ala—D-Glu-D-Glu-D-Val-D-Val-D-Glu-D-Lys-D-Lys-D-Glu-D-Lys-D-Leu-D-Asp-D-Lys-D—Thr-D-Thr-D-Ile-D-Glu-D-Ser-D-Ser-D-Thr-D-Asp-D-Val-D-Ala-D-Ala-D-Asp-D-Ser—OH (SEQ ID NO:1) as a white powder. FAB mass spectrometry indicated that the peptide has molecular weight (MW) of [M+H].sup.+=3067 (calculated MW=3066.3). Amino acid analysis from 6 N HCl hydrolysates (110.degree.C., 24 hours) revealed the amino acid composition values: Asp, 3.9(4); Glu, 5.7(6); Ser, 2.8(3); Thr, 2.9(3); Ala, 2.9(3) Val, 2.1(3); Ile, 0.9(1); Leu, 0.9(1); Lys, 4.2(4). The value 2.9 of valine was revealed at 120 hours acid hydrolysis. Aspartic acid values are the sum of their acids and amides. Numbers given in parentheses are the expected number of residues in the peptide.

EXAMPLE 2

Native/retro-inverso Thymosin Alpha 1 Hybrids:

Native/retro-inverso thymosin alpha 1 hybrid was synthesized, in analogy to routine Fmoc-SPPS (solid phase peptide synthesis), by the stepwise addition of base labile Fmoc-amino protected amino acids to PEG (polyethylene glycol) polystyrene solid support. 1.0 gm of NovaSyn TGA resin (0.23 mmol/g) (Novabiochem, San Diego, Calif.) was suspended to swell for 60 minutes at room temperature in a peptide synthesis flask in 15 volumes of 100% DMF and then washed with 100% DCM. A modified 1-(2-mesitylene-sulfonyl)-3-nitro-1,2,4-triazole (MSNT)/1-methylimidazole (NMI) coupling method (Blankemeyer-Menge et al., *Tetrahedron Lett.*, 31:1701, 1990) and double coupling were applied for the attachment of the first Fmoc-amino acid derivative to the NovaSyn TGA resin. The NovaSyn TGA resin was allowed to react with 0.5 mmol (2.5 equivalent relative to resin 0.2 mmol) of Fmoc-D-Ser(But)-OH (0.19 gm), 0.5 mmol of MSNT (0.15 gm), 0.4 mmol of NMI (0.033 gm) in DCM for 2 hours in the first coupling, then overnight in the second coupling with agitation in a mechanical shaker to form Fmoc-D-Ser(But)-NovaSyn TGA resin. After end-capping unreacted hydroxyl groups with acetic anhydride and pyridine for 30 minutes at room temperature, the amino acid resin was then washed 3 times with DCM and 3 times with DMF. The solid phase peptide synthesis was then performed in the following steps wherein in accordance with the desired sequence one amino acid was successively coupled to the resin-bound amino acid or the growing peptide chain on the resin in each synthetic cycle. Fmoc-amino acid corresponds to the N-terminal amino acid. Fmoc-amino acids, whose amino group, carboxyl group and/or hydroxyl group is protected with appropriate protective groups, are activated at its alpha carboxyl group by creating the HOBt ester in situ with HOBt and DIC or HBTU in DMF or NMP. One hour coupling times and double coupling were used in all amino acid couplings. 15 volumes of solvent or reagents were used for each washing. All amino acid derivatives used were as indicated:

1. Wash twice with 100% DMF;
2. Stir for 5 minutes with 25% piperidine in DMF;
3. Stir for 20 minutes with 25% piperidine in DMF;
4. Wash twice with 100% DMF;
5. Wash twice with 100% DCM;
7. Wash twice with 100% DMF;
8. Stir for 60 minutes with 2.0 mmol each of Fmoc-D-Asp(OBUt)-OH, HOBt, and DIC NMP;
9. Stir for 60 minutes with 2.0 mmol each of Fmoc-D-Asp(OBUt)-OH, HOBt, and HBTU, and DIPEA in NMP;
10. Wash twice with 100% DMF;
11. Wash twice with 100% DCM;
12. The coupling reaction was monitored for completeness in each cycle of addition by Kaiser test (ninhydrin color reaction) (Sarin et al., Analytical Biochemistry, 117:147, 1981) to determine free amine. If the reaction shows positive (blue color), repeat steps 8–12; if no color, go to the next cycle.

The peptide chain elongation cycle was continued in the same manner by using Fmoc-amino acids and one amino acid was incorporated into the growing peptide at a time in step 8 of each synthetic cycle in the following order: Fmoc-D-Ala-OH.H$_2$O, Fmoc-D-Ala-OH.H$_2$O, Fmoc-D-Val-OH, Fmoc-D-Asp(OBut)-OH, Fmoc-D-Thr(But)-OH, Fmoc-D-Ser(But)-OH, Fmoc-D-Ser(But)-OH, Fmoc-D-Glu(OBut)-OH, Fmoc-D-Ile-OH, Fmoc-D-Thr(But)-OH, Fmoc-D-Thr(But)-OH, Fmoc-D-Lys(Boc)-OH, Fmoc-D-Asp(OBut)-OH, Fmoc-D-Leu-OH, Fmoc-D-Lys(Boc)-OH, Fmoc-D-Glu(OBut)-OH, Fmoc-D-Lys(Boc)-OH, Fmoc-D-Lys(Boc)-OH, Fmoc-D-Glu(OBut)-OH, Fmoc-D-Val-OH, Fmoc-D-Val-OH, Fmoc-D-Glu(OBut)-OH, Fmoc-D-Glu(OBut)-OH, Fmoc-D-Ala-OH.H$_2$O, Fmoc-D-Glu(OBut)-OH, Fmoc-D-Asn(Trt)-OH, Fmoc-Ser(But)-OH, Fmoc-Gly-OH, Fmoc-Gly-OH, Fmoc-Gly-OH, Fmoc-Gly-OH, Fmoc-Ser(But)-OH, Fmoc-Asn(Trt)-OH, Fmoc-Glu(OBut)-OH, Fmoc-Ala-OH.H$_2$O, Fmoc-Glu(OBut)-OH, Fmoc-Glu(OBut)-OH, Fmoc-Val-OH, Fmoc-Val-OH, Fmoc-Glu(OBut)-OH, Fmoc-Lys(Boc)-OH, Fmoc-Lys(Boc)-OH, Fmoc-Glu(OBut)-OH, Fmoc-Lys(Boc)-OH, Fmoc-Leu-OH, Fmoc-Asp(OBut)-OH, Fmoc-Lys(Boc)-OH, Fmoc-Thr(But)-OH, Fmoc-Thr(But)-OH, Fmoc-Ile-OH, Fmoc-Glu(OBut)-OH, Fmoc-Ser(But)-OH, Fmoc-Ser(But)-OH, Fmoc-Thr(But)-OH, Fmoc-Asp(OBut)-OH, Fmoc-Val-OH, Fmoc-Ala-OH.H$_2$O, Fmoc-Ala-OH.H$_2$O, Fmoc-Asp(OBut)-OH, Fmoc-Ser(But)-OH and CH$_3$COOH. After completion of the final coupling reaction, the N$^\alpha$ deprotection reaction was carried out by stirring the protected native/retro-inverso thymosin alpha 1 hybrid NovaSyn TGA resin with 25% piperidine in DMF for 30 minutes. Cleavage and deblocking of the side chains of the retro-inverso-TM-alpha1 was accomplished with 94% TFA, 4% TIS in distilled water in two steps: (1) for 30 minutes at room temperature to release the protected peptide from the resin, and (2) for another 4 hours to remove the side-chain protected groups from the peptide after it was separated from the resin by filtration (0.22 .mu.m filter).The cleaved peptide was then precipitated by using 10 times volumetric excess of cold ether. The precipitated peptide was washed several times with ether and allowed to dry. Crude peptides are subjected to gel filtration followed by HPLC purification. Native/retro-inverso thymosin alpha 1 hybrid was purified by semi-preparative HPLC on a 25 cm octadecyl silane column (Vydac, Hisperia, Calif.) to give 90 mg of Ac-Ser-Asp-Ala—Ala-Val-Asp-Thr-Ser-Ser-Glu-Ile-Thr-Thr-Lys-Asp-Leu-Lys-Glu-Lys-Lys-Glu-Val-Val—Glu-Glu-Ala-Glu-Asn-Ser-Gly-Gly-Gly-Gly-Ser-D-Asn-D-Glu-D-Ala-D-Glu-D-Glu-D—Val-D-Val-D-Glu-D-Lys-D-Lys-D-Glu-D-Lys-D-Leu-D-Asp-D-Lys-D-Thr-D-Thr-D—Ile-D-Glu-D-Ser-D-Ser-D-Thr-D-Asp-D-Val-D-Ala-D-Ala-D-Asp-D-Ser-OH (SEQ ID NO:2) as a white powder. FAB mass spectrometry indicated that the peptide has molecular weight (MW) of [M+H]$^+$=6157 (calculated MW=6156.6). Amino acid analysis from 6 N HCl hydrolysates (110.degree.C., 24 hours) revealed the amino acid composition values: Asp, 8.4(8); Glu, 12.3(12); Ser, 5.6(6); Thr, 5.9(6); Ala, 6.3(6); Val, 4.3(6); Ile, 2.1(2); Leu, 1.9(2); Lys, 7.7(8). The value 6.2 of valine was revealed at 120 hours acid hydrolysis. Aspartic acid values are the sum of their acids and amides. Numbers given in parentheses are the expected number of residues in the peptide.

I claim:

1. A peptide having an amino acid sequence (SEQ ID NO:2) of Ser-Asp-Ala-Ala-Val-Asp-Thr-Ser-Ser—Glu-Ile-Thr-Thr-Lys-Asp-Leu-Lys-Glu-Lys-Lys-Glu-Val-Val-Glu-Glu-Ala-Glu-Asn—Asn-Glu-Ala-Glu-Glu-Val-Val-Glu-Lys-Lys-Glu-Lys-Leu-Asp-Lys-Thr-Thr-Ile-Glu-Ser—Ser-Thr-Asp-Val-Ala-Ala-Asp-Ser in all-D, all-L, or partial D configuration.

2. A peptide having an amino acid sequence (SEQ ID NO:1) of Asn-Glu-Ala-Glu-Glu-Val-Val-Glu-Lys—Lys-Glu-Lys-Leu-Asp-Lys-Tbr-Thr-Ile-Glu-Ser-Ser-Thr-Asp-Val-Ala-Ala-Asp-Ser in all-D or all-L configuration.

* * * * *